United States Patent [19]

Cherkofsky

[11] Patent Number: 4,477,463
[45] Date of Patent: Oct. 16, 1984

[54] ANTIINFLAMMATORY AND/OR ANALGESIC 1-ALKYL-4,5-DIARYL-2-FLUOROALKYL-1H-PYRROLES

[75] Inventor: Saul C. Cherkofsky, Wilmington, Del.

[73] Assignee: E. I. Du Pont de Nemours and Company, Wilmington, Del.

[21] Appl. No.: 376,650

[22] Filed: May 10, 1982

[51] Int. Cl.$^3$ .................. C07D 207/32; C01D 403/04; A61K 31/44; A61K 31/40
[52] U.S. Cl. .................... 424/274; 424/263; 548/560; 546/281
[58] Field of Search ............. 548/561, 562, 560; 424/274, 263; 546/281

[56] References Cited

U.S. PATENT DOCUMENTS

| | | | |
|---|---|---|---|
| 3,707,475 | 12/1972 | Lombardino | 260/309 |
| 3,709,906 | 1/1973 | Yoshida et al. | 260/326.5 |
| 3,758,515 | 7/1969 | Archibald et al. | 548/561 |
| 4,168,315 | 9/1979 | Rynbrandt et al. | 424/270 |
| 4,267,189 | 5/1981 | Cherkofsky | 548/560 |
| 4,318,917 | 3/1982 | Cherkofsky et al. | 424/274 |
| 4,335,136 | 6/1982 | Cherkofsky | 546/281 |

OTHER PUBLICATIONS

Jones et al, The Chem. of Pyrroles, Academic Press, N.Y. N.Y., pp. 144–146 (1977).
Cantacuzène, et al., "Condensation of Perfluoroalkyl Iodides with Unsaturated Nitrogen Compounds", J. Chem. Soc. I, 12, pp. 365-1371 (1977).

*Primary Examiner*—Alton D. Rollins
*Assistant Examiner*—D. B. Springer

[57] ABSTRACT

Antiinflammatory and/or analgesic 1-alkyl-4,5-diaryl-2-fluoroalkyl-1H-pyrroles, such as 4,5-bis(4-methoxyphenyl)-1-methyl-2-trifluoromethyl-1H-pyrrole, useful for treating arthritis and related diseases and/or relieving pain.

10 Claims, No Drawings

ANTIINFLAMMATORY AND/OR ANALGESIC 1-ALKYL-4,5-DIARYL-2-FLUOROALKYL-1H-PYRROLES

BACKGROUND OF THE INVENTION

This invention relates to antiinflammatory and/or analgesic pyrroles.

Yoshida et al., in U.S. Pat. No. 3,709,906 and other references including *Experientia*, 28, (8) 937 (1972) and *Yakugaku Zasshi*, 92, 1 (1972); 92, 11 (1972); 92, 305 (1972); 92, 311 (1972); and 93, 584 (1973) disclose 5-alkyl-2,3-diarylpyrroles, including 2,3-bis(4-methoxyphenyl)-5-methyl-1H-pyrrole ("bimetopyrol"), which are useful as antiinflammatory agents.

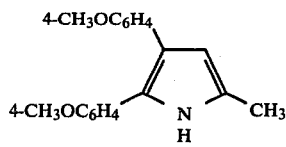

Cherkofsky, in U.S. Pat. No. 4,267,190 discloses 4,5-diaryl-α,α-bis(polyfluoromethyl)-1H-pyrrole-2-methanethiols, which are useful as antiinflammatory agents.

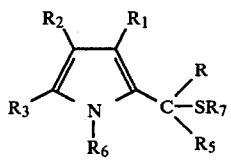

R. W. Guy and R. Alan Jones, *Aust. J. Chem.*, 19, 1871 (1966) describe the synthesis of 2,3-diphenyl-5-methyl-1H-pyrrole.

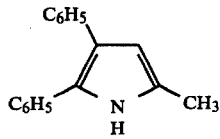

A. Laurent et al., *Tetrahedron Letters*, 18, 1587 (1979) describe the synthesis of 4,5-dimethyl-2,3-diphenyl-1H-pyrrole.

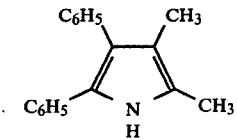

D. Cantacuzène et al., J. Chem. Soc. Perkin Trans. I, 12, 1365 (1977) describe the reaction of N-methylpyrrole with various perfluoroalkyl iodides to give 1-methyl-2-perfluoroalkyl-1H-pyrroles.

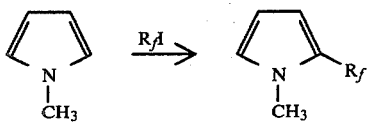

Belgian Patent No. 870,851 discloses 4,5-diaryl-2-trifluoromethylthiazoles, which are useful as platelet aggregation inhibitors.

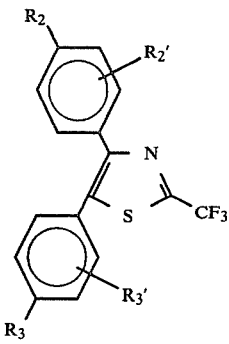

There is a continuing need for safe and effective antiinflammatory agents to treat inflammation, a disease process characterized by redness, fever, swelling, and pain. Arthritis, in its various forms, is the most prevalent, chronic, and severe of the inflammatory diseases. Traumatic injury and infection also involve inflammation, and antiinflammatory drugs are often used in their treatment as well.

The usefulness of many commercial antiinflammatories, however, is limited because of toxicity and adverse side-effects. Many produce gastric irritation and can cause changes in blood cells or can affect the central nervous system. Adreno-cortical steroids, for example, produce gastric irritation and suppression of normal adrenal function.

The present invention results from efforts to develop new anti-arthritic compounds with good antiinflammatory activity and minimal side effects that could be more effective in treating arthritis than are presently available drugs. In addition to antiinflammatory properties, some compounds of this invention have demonstrated analgesic activity in a test procedure. This additional property is desirable in treatment of arthritis or related diseases; however, such compounds can be employed solely to alleviate pain.

SUMMARY OF THE INVENTION

This invention relates to compounds of Formula I, pharmaceutical compositions containing them, and methods of use of these compounds to treat arthritis and relieve inflammation and/or relieve pain in mammals.

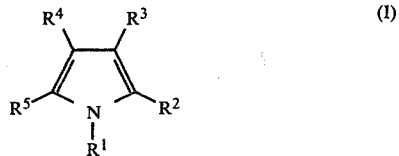

wherein
R$^1$ is methyl or ethyl;
R$^2$ is CF$_3$ or CF$_2$CF$_3$;
R$^3$ is H, methyl, or ethyl; and
R$^4$ and R$^5$ independently are pyridyl or 4—XC$_6$H$_4$— where X is H, F, Cl, Br, R$^6$, R$^6$S(O)$_n$, R$^6$O, or R$^6$R$^7$N where R$^6$ and R$^7$ independently are methyl or ethyl and n=0, 1 or 2;
provided that:
(1) R$^4$ and R$^5$ cannot both be 4—FC$_6$H$_4$—;

(2) $R^4$ and $R^5$ cannot both be $C_6H_5-$; and
(3) $R^4$ cannot be $4-FC_6H_4-$ when $R^5$ is $4-CH_3OC_6H_4$;
or a pharmaceutically suitable salt of a compound of Formula (I) when $R^4$ or $R^5$ is pyridyl or $4-R^6R^7NC_6H_4-$.

PREFERRED COMPOUNDS

Preferred compounds of Formula (I) are those where:
$R^3 = H$; and
$R^4$ and $R^5$ independently are $4-XC_6H_4-$ where $X = CH_3O$, F, or $CH_3S(O)_n$ where $n = 0$, 1 or 2.

More preferred compounds of Formula (I) are those where:
$R^1 = $ methyl;
$R^2 = CF_3$ or $CF_2CF_3$;
$R^3 = H$; and
$R^4$ and $R^5$ independently are $4-XC_6H_4-$ where $X = CH_3O$, F or $CH_3S(O)_n$ where $n = 0$, 1 or 2.

Examples of compounds that are specifically preferred are:
(1) 4,5-bis(4-methoxyphenyl)-1-methyl-2-trifluoromethyl-1H-pyrrole;
(2) 4,5-bis(4-methoxyphenyl)-1-methyl-2-pentafluoroethyl-1H-pyrrole;
(3) 4-(4-fluorophenyl)-1-methyl-5-(4-methylthiophenyl)-2-trifluoromethyl-1H-pyrrole;
(4) 4-(4-fluorophenyl)-1-methyl-5-(4-methylsulfonylphenyl)-2-trifluoromethyl-1H-pyrrole; and
(5) 1-methyl-4,5-bis(4-methylthiophenyl)-2-trifluoromethyl-1H-pyrrole.

Pharmaceutically suitable salts and their preparation are well known to those skilled in pharmaceuticals and any can be used in the present invention. Suitable salts of compounds where either $R^4$ or $R^5$ is pyridyl or $4-R^6R^7NC_6H_4-$ include pharmaceutically suitable acid addition salts, preferably formed from mineral acids, and include hydrochloride, nitrate, and sulfate. The acid used preferably has a p$K_a$ of not greater than 2.5.

SYNTHESIS

The compounds of this invention can be prepared from 1-alkyl-2,3-diarylpyrroles, methods for the preparation of which are described in U.S. Pat. No. 4,267,190.

Reaction of a 1-alkyl-2,3-diarylpyrrole with a perfluoroalkyl iodide such as trifluoromethyl iodide or pentafluoroethyl iodide, in a pressure vessel at a high temperature, generally from 125° to 200° C., either neat or in the presence of a high boiling polar solvent, such as dimethylformamide, in the presence or absence of a hindered amine, such as ethyl diisopropylamine, gives a compound of Formula I.

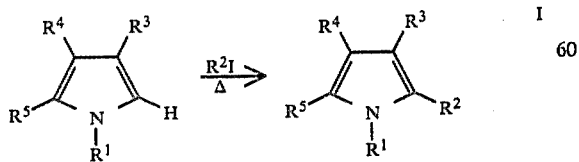

The preparation of these compounds is further illustrated by the following examples in which all temperatures are in degrees Centigrade.

EXAMPLE 1

4,5-Bis(4-methoxyphenyl)-1-methyl-2-trifluoromethyl-1H-pyrrole

A. 2,3-Bis(4-methoxyphenyl)-1-methyl-1H-pyrrole

To 400 ml of DMSO under nitrogen was added with stirring 7.5 g (0.15 mole) of 50% sodium hydride dispersion in mineral oil. After the mixture was stirred for an hour, a solution of 27.9 g (0.1 mole) of 2,3-bis(4-methoxyphenyl)-1H-pyrrole[(1)] in 100 ml DMSO was added, keeping the temperature of the reaction below 20° with ice cooling as necessary. The mixture was stirred at room temperature another two hours, then 28.4 g (0.2 mole) of methyl iodide was added dropwise. The mixture was stirred overnight at room temperature, then 50 ml of water was added cautiously dropwise. The mixture was then poured into 2 l ice water and extracted three times with ether. The ether extracts were washed three times with water, then were dried and concentrated to give 21.5 g of crude product. This material was combined with another 2.2 g of solid product isolated by filtration of the aqueous layer. The combined crude product was purified by chromatography on 800 g of silica gel, eluting with toluene, to give, after trituration with hexane, 10.3 g (35%) of off-white solid, m.p. 126°–127°

(1) J. Szmuszkowicz et al., *J. Med Chem.*, 9, 527 (1966).

Anal. Calcd. for $C_{19}H_{19}NO_2$: C, 77.79; H, 6.53; N, 4.77. Found: C, 77.6; H, 6.4; N, 4.7; 77.6; 6.6; 4.8.

B. 4,5-Bis(4-methoxyphenyl)-1-methyl-2-trifluoromethyl-1H-pyrrole

In a pressure reaction vessel was placed 2.9 g (0.01 mole) of 2,3-bis(4-methoxyphenyl)-1-methyl-1H-pyrrole and 1.3 g (0.01 mole) of ethyl diisopropylamine. The vessel was cooled and evacuated, and 2.0 g (0.01 mole) of trifluoromethyl iodide was added. The mixture was heated at 150° for approximately 18 hours. The vessel was cooled and vented, and the contents rinsed out with methylene chloride. The methylene chloride solution was washed with water three times then dried and concentrated to give the crude product. This was purified by chromatography on 400 g silica gel, eluting with toluene, to give after recrystallization from hexane, 1.0 g (28%) of product as a white solid, m.p. 125°–126°.

Anal. Calcd. for $C_{20}H_{18}F_3NO_2$: C, 66.47; H, 5.02; N, 3.87. Found: C, 66.6; H, 4.9; N, 4.1; 66.6; 5.0; 4.0.

Other 1-alkyl-4,5-diaryl-2-fluoroalkyl-1H-pyroles prepared by the procedures described are illustrated in Table I.

TABLE I

| Ex. | $R^1$ | $R^2$ | $R^4$ | $R^5$ | m.p. (°C.) |
|---|---|---|---|---|---|
| 1 | $CH_3$ | $CF_3$ | $4-CH_3OC_6H_4$ | $4-CH_3OC_6H_4$ | 126–127° |
| 2 | $CH_3$ | $CF_2CF_3$ | $4-CH_3OC_6H_4$ | $4-CH_3OC_6H_4$ | 104–105° |
| 3 | $CH_2CH_3$ | $CF_3$ | $4-CH_3OC_6H_4$ | $4-CH_3OC_6H_4$ | oil |
| 4 | $CH_3$ | $CF_3$ | $4-ClC_6H_4$ | $4-ClC_6H_4$ | 139– |

TABLE I-continued

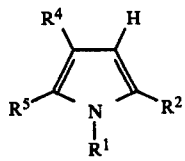

| Ex. | $R^1$ | $R^2$ | $R^4$ | $R^5$ | m.p. (°C.) |
|---|---|---|---|---|---|
| 5 | $CH_3$ | $CF_3$ | $4\text{-}CH_3C_6H_4$ | $4\text{-}CH_3C_6H_4$ | 140° 152–154° |
| 6 | $CH_3$ | $CF_3$ | $4\text{-}FC_6H_4$ | $4\text{-}CH_3SC_6H_4$ | 121–122° |
| 7 | $CH_3$ | $CF_3$ | $4\text{-}FC_6H_4$ | $4\text{-}CH_3SO_2C_6H_4$ | 159–160° |
| 8 | $CH_3$ | $CF_3$ | $4\text{-}CH_3SC_6H_4$ | $4\text{-}CH_3SC_6H_4$ | 113–114° |

Other 1-alkyl-4,5-diaryl-2-fluoroalkyl-1H-pyrroles that can be prepared by the procedures described are illustrated in Table II.

TABLE II

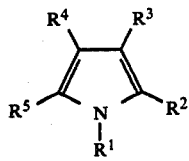

| Ex. | $R^1$ | $R^2$ | $R^3$ | $R^4$ | $R^5$ |
|---|---|---|---|---|---|
| 9 | $CH_3$ | $CF_3$ | $CH_3$ | $4\text{-}CH_3OC_6H_4$ | $4\text{-}CH_3OC_6H_4$ |
| 10 | $CH_3$ | $CF_3$ | $CH_2CH_3$ | $4\text{-}FC_6H_4$ | $4\text{-}CH_3SC_6H_4$ |
| 11 | $CH_3$ | $CF_3$ | H | $4\text{-}FC_6H_4$ | 3-pyridyl |
| 12 | $CH_3$ | $CF_3$ | H | $4\text{-}FC_6H_4$ | 2-pyridyl |
| 13 | $CH_3$ | $CF_3$ | H | $4\text{-}FC_6H_4$ | 4-pyridyl |
| 14 | $CH_3$ | $CF_3$ | H | $C_6H_5$ | $4\text{-}CH_3OC_6H_4$ |
| 15 | $CH_3$ | $CF_3$ | H | $4\text{-}BrC_6H_4$ | $4\text{-}CH_3SC_6H_4$ |
| 16 | $CH_3$ | $CF_3$ | H | $4\text{-}CH_3CH_2C_6H_4$ | $4\text{-}CH_3CH_2C_6H_4$ |
| 17 | $CH_3$ | $CF_3$ | H | $4\text{-}FC_6H_4$ | $4\text{-}CH_3CH_2SC_6H_4$ |
| 18 | $CH_3$ | $CF_3$ | H | $4\text{-}CH_3CH_2OC_6H_4$ | $4\text{-}CH_3CH_2OC_6H_4$ |
| 19 | $CH_3$ | $CF_3$ | H | $4\text{-}FC_6H_4$ | $4\text{-}(CH_3)_2NC_6H_4$ |
| 20 | $CH_3$ | $CF_3$ | H | $4\text{-}FC_6H_4$ | $4\text{-}(CH_3CH_2)_2NC_6H_4$ |
| 21 | $CH_3$ | $CF_3$ | H | $4\text{-}FC_6H_4$ | $4\text{-}CH_3S(O)C_6H_4$ |

Dosage Forms

The antiinflammatory and/or analgesic agents of this invention can be administered to treat inflammation and/or relieve pain by any means that produces contact of the active agent with the agent's site of action in the body of a mammal. They can be administered by any conventional means available for use in conjunction with pharmaceuticals; either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.1 to 100 milligrams per kilogram of body weight. Ordinarily 0.5 to 50, and preferably 1 to 25 milligrams per kilogram per day given in divided doses 1 to 6 times a day or in sustained release form is effective to obtain desired results.

Dosage forms (compositions) suitable for internal administration contain from about 1 milligram to about 500 milligrams of active ingredient per unit. In these pharmaceutical compositions the active ingredient will ordinarily by present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions, it can also be administered parenterally, in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Some of the compounds of this invention form salts. Solutions for parenteral administration of these compounds contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition parenteral solutions can contain perservatives, such as benzalkonium chloride, methyl- or propyl-paraben, and chlorobutanol.

Suitable pharmaceutical carriers are described in Remingtons's Pharmaceutical Sciences, E. W. Martin, a standard reference text in this field.

Useful pharmaceutical dosage forms for administration of the compounds of this invention can be illustrated as follows:

Capsules

A large number of unit capsules are prepared by filling standard two-piece hard gelatin capsules each with 75 milligrams of powdered active ingredient, 150 milligrams of lactose, 24 milligrams of talc, and 6 milligrams magnesium stearate.

Soft Gelatin Capsules

A mixture of active ingredient in soybean oil is prepared and injected by means of a positive displacement pump into gelatin to form soft gelatin capsules containing 75 milligrams of the active ingredient. The capsules are washed in petroleum ether and dried.

Tablets

A large number of tablets are prepared by conventional procedures so that the dosage unit is 75 milligrams of active ingredient, 6 milligrams of magnesium stearate, 70 milligrams of microcrystalline cellulose, 11 milligrams of cornstarch and 200 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is sterilized by commonly used techniques.

Suspension

An aqueous suspension is prepared for oral administration so that each 5 milliliters contain 25 milligrams of finely divided active ingredient, 200 milligrams of sodium carboxymethyl cellulose, 5 milligrams of sodium benzoate, 1.0 grams of sorbitol solution, U.S.P., and 0.025 milliliters of vanillin.

Injectable

A parenteral composition suitable for administration by injection is prepared by dissolving 1% by weight of active ingredient in sodium chloride injection U.S.P. XX and adjusting the pH of the solution to between 6 and 7. The solution is sterilized by commonly used techniques.

Use

To detect and compare the antiinflammatory activities of compounds in this series and standard drugs, a test was used based on a standard model of arthritis for which there is good correlation with human efficacy. The model is adjuvant-induced arthritis in rats. *Federation Proceedings*, Vol. 32, No. 2, 1973 "Models Used for the Study and Therapy of Rheumatoid Arthritis'-'—Symposium of the American Society for Pharmacology and Experimental Therapeutics—states "The rat polyarthritis produced by intradermal injection of a suspension of *Mycobacterium tuberculosis* in mineral oil (adjuvant) has been used extensively for the screening of drugs of potential use in rheumatoid arthritis."

Established Adjuvant-Induced Arthritis in Rats

Charles River Lewis male rats (130–150 grams) are injected subcutaneously in the plantar area of the right hind paw with 0.1 ml of adjuvant (Difco heat-killed, lyophilized *Mycobacterium butyricum* suspended in mineral oil 5 mg/ml). 20 Non-arthritic controls are injected with mineral oil. The animals are held for 2 weeks to allow development of arthritis. Paw volumes (uninjected, left hind paw) are measured and the adjuvant-injected rats are culled and distributed to treatment groups of 10 of equal disease severity. Non-arthritic controls are distributed to 2 groups of 10. The rats are given oral doses of compound or PVA-Acacia (Polyvinyl Alcohol 1%, Gum acacia, U.S.P. 5%, Methylparaben 0.5%) (10 ml/kg) by gavage on that day and on the 6 following days. One day after the last dose the paw volumes (uninjected, left hind paw) are measured using a Ugo Basile Volume Differential Meter Model 7101.

$$\frac{\text{Arthritic Control} - \text{Treatment Group}}{\text{Mean Paw Volume (ml)} - \text{Mean Paw Volume (ml)}} \times 100 =$$
$$\frac{\text{Arthritic Control}}{\text{Mean Paw Volume (ml)}} - \frac{\text{Non-Arthritic Control}}{\text{Mean Paw Volume (ml)}}$$

% Decrease from Control Mean Paw Volume.

Dose-response regression lines of the percent decrease are plotted on semi-log paper by visual fit and the ED50% decrease from control paw volume is determined by inspection. Data for some of the compounds of this invention are summarized in Table III.

Compounds from this series were also compared to indomethacin, phenylbutazone, ibuprofen, and aspirin.

Phenylquinone Writhing Test

A standard procedure for detecting and comparing the analgesic activity of compounds in this series for which there is a good correlation with human efficacy is the standard phenylquinone writhing test modified from Siegmund, et al., *Proc. Soc. Exp. Biol. Med.*, 95, 729 (1957). A test compound suspended in 1% methylcellulose was given orally to fasted (17–21 hours) female white mice, 5–20 animals per double blind test. Aqueous (0.01% phenyl-p-benzoquinone) phenylquinone, 0.20 ml per mouse, was injected intraperitoneally 6 minutes before observations were begun. At an appropriate time after the oral administration of the test compound, the mice were observed for 10 minutes for a characteristic stretching or writhing syndrome which is indicative of pain induced by phenylquinone. The effective analgesic dose for 50% of the mice ($ED_{50}$) was calculated by the moving average method of Thompson, W. R., *Bact. Rev.*, 11, 115–145 (1947); the time of peak activity was determined for many of the compounds. Data for some of the compounds are summarized in Table III together with data for some standard analgetic-antiinflammatory drugs.

TABLE III

| | Biological Activity | |
|---|---|---|
| Example | Adjuvant Arthritic $ED_{50}$ (mg/kg) | Phenylquinone Writhing (PQW) $ED_{50}$ (mg/kg) |
| 1 | 1.25 | 16 |
| 2 | (32% at 9)[1] | 1.8 |
| 3 | 18 | 47 |
| 4 | (29% at 9)[1] | NT[2] |
| 5 | (28% at 9)[1] | 18 |
| 6 | 1.8 | 16 |
| 7 | 3.5 | NT[2] |
| 8 | 1.8 | >108 |
| Indomethacin | 0.3 | 0.35 |
| Phenylbutazone | 10 | 80 |
| Ibuprofen | 100 | 10 |

TABLE III-continued

| | Biological Activity | |
|---|---|---|
| Example | Adjuvant Arthritic ED$_{50}$ (mg/kg) | Phenylquinone Writhing (PQW) ED$_{50}$ (mg/kg) |
| Aspirin | 305 | 135 |

[1] Values in parenthesis indicate the percent reduction in paw volume at the indicated dose.
[2] NT indicates not tested.

"Consisting essentially of" in the present disclosure is intended to have its customary meaning: namely, that all specified material and conditions are very important in practicing the invention but that unspecified materials and conditions are not excluded so long as they do not prevent the benefits of the invention from being realized.

What is claimed is:

1. A compound having the formula:

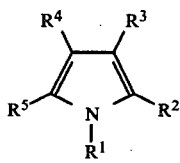

wherein
$R^1$ is methyl or ethyl;
$R^2$ is $CF_3$ or $CF_2CF_3$;
$R^3$ is H, methyl, or ethyl; and
$R^4$ and $R^5$ independently are pyridyl or 4—$XC_6H_4$— where X is H, F, Cl, Br, $R^6$, $R^6S(O)_n$, $R^6O$, or $R^6R^7N$ where $R^6$ and $R^7$ independently are methyl or ethyl and n=0 or 2;
provided that:
(1) $R^4$ and $R^5$ cannot both be 4—$FC_6H_4$—;
(2) $R^4$ and $R^5$ cannot both be $C_6H_5$—; and
(3) $R^4$ cannot be 4—$FC_6H_4$— when $R^5$ is 4—$CH_3OC_6H_4$;
or a pharmaceutically suitable salt of a compound of Formula (I) when $R^4$ or $R^5$ is pyridyl or 4—$R^6R^7NC_6H_4$—.

2. Compounds of claim 1 wherein:
$R^3$=H; and
$R^4$ and $R^5$ independently are 4—$XC_6H_4$— where X=$CH_3O$, F, or $CH_3S(O)_n$ where n=0, 1 or 2.

3. Compounds of claim 1 wherein:
$R^1$=methyl;
$R^2$=$CF_3$ or $CF_2CF_3$;
$R^3$=H; and
$R^4$ and $R^5$ independently are 4—$XC_6H_4$— where X=$CH_3O$, F or $CH_3S(O)_n$ where n=0, 1 or 2.

4. The compound of claim 1 which is 4,5-bis(4-methoxyphenyl)-1-methyl-2-trifluoromethyl-1H-pyrrole.

5. The compound of claim 1 which is 4,5-bis(4-methoxyphenyl)-1-methyl-2-pentafluoroethyl-1H-pyrrole.

6. The compound of claim 1 which is 4-(4-fluorophenyl)-1-methyl-5-(4-methylthiophenyl)-2-trifluoromethyl-1H-pyrrole.

7. The compound of claim 1 which is 4-(4-fluorophenyl)-1-methyl-5-(4-methylsulfonylphenyl)-2-trifluoromethyl-1H-pyrrole.

8. The compound of claim 1 which is 1-methyl-4,5-bis(4-methylthiophenyl)-2-trifluoromethyl-1H-pyrrole.

9. A pharmaceutical composition consisting essentially of a suitable pharmaceutical carrier and an effective antiinflammatory or analgesic amount of a compound of claim 1, 2, 3, 4, 5, 6, 7, or 8.

10. A method of treating inflammation, pain or both in a mammal which comprises administering to the mammal an effective antiinflammatory or analgesic amount of at least one compound of claim 1, 2, 3, 4, 5, 6, 7, or 8.

* * * * *